United States Patent [19]

Findl et al.

[11] 4,242,447
[45] Dec. 30, 1980

[54] RAPID DETECTION OF BACTERIA

[75] Inventors: Eugene Findl, Amityville; Leonard D. Kurtz, Woodmere, both of N.Y.

[73] Assignee: BioResearch, Farmingdale, N.Y.

[21] Appl. No.: 964,622

[22] Filed: Nov. 29, 1978

[51] Int. Cl.$^3$ ............................................. C12Q 1/06
[52] U.S. Cl. ...................................... 435/39; 435/18; 435/22; 435/291; 435/808
[58] Field of Search ...................... 435/18, 22, 29, 30, 435/34, 38, 39, 291, 292, 293, 316, 808; 250/461 B

[56] References Cited

U.S. PATENT DOCUMENTS

| | | | |
|---|---|---|---|
| 3,551,295 | 12/1970 | Dyer | 435/18 X |
| 3,586,859 | 6/1971 | Katz | 250/461 B |
| 3,779,907 | 12/1973 | Li et al. | 210/23 R X |
| 3,864,571 | 2/1975 | Stillman et al. | 250/461 B |
| 3,870,601 | 3/1975 | Warren et al. | 435/34 X |
| 3,887,812 | 6/1975 | Hirschfeld | 250/461 B |
| 3,916,197 | 10/1975 | Fulwyler | 250/461 B |
| 3,957,584 | 5/1976 | Kronish et al. | 435/18 X |
| 4,025,393 | 5/1977 | Hirschfeld | 435/34 |
| 4,070,247 | 1/1978 | Burt | 435/38 |
| 4,126,516 | 11/1978 | Messing et al. | 435/34 |

OTHER PUBLICATIONS

William Jakoby, Editor, Methods in Enzymology, vol. 22, pp. 86-95, 1971.
H. R. Renel et al., Nat. Academy of Sciences Proceedings, vol. 47, pp. 1956-1967, 1961.
William J. Asher et al., "Exxon Company Report AK-1-73-2224", 1974.
Raam R. Mohan et al., Biotech and Bioengineering, vol. XVII, pp. 1137-1156, 1975.

Primary Examiner—Robert J. Warden
Attorney, Agent, or Firm—Larson, Taylor and Hinds

[57] ABSTRACT

Bacteria, particularly coliform bacteria, present in a liquid, are rapidly detected. A sample of the liquid to be tested is admixed with an enzyme-inducing agent which induces the production of an enzyme in the bacteria, the enzyme being capable of reacting with a fluorescent conjugate ingested by the bacteria to release its fluorescent portion. Conditions are controlled such that a sufficient number of molecules of enzyme are produced per bacterium present in the liquid sample to effect release of the fluorescent portion. A fluorescent conjugate, capable of being ingested by the bacteria, is admixed with the liquid sample for reaction with the enzyme to release the fluorescent portion of the fluorescent conjugate. The liquid sample is then formed into microdroplets in a liquid carrier such that the fluorescent material is retained in the microdroplets. A liquid carrying the microdroplets is formed into a stream in which the microdroplets become aligned and the stream is moved relative to a detector for detecting fluorescence. The detected fluorescence provides a measure of the quantity of bacteria in the liquid sample. By proceeding in this manner, it is possible to quantify the bacteria, at a level down to two per ml, in less than two hours. Apparatus suitable for the method is also disclosed.

15 Claims, 2 Drawing Figures

RAPID DETECTION OF BACTERIA

The Government has rights in this invention pursuant to Contract N00014–713 awarded by the Department of the Navy

BACKGROUND OF THE INVENTION

The present invention relates to the rapid quantification of bacteria, in particular, of coliform bacteria.

Nearly all water sources contain a wide variety of bacterial contaminants, the great majority of which are not harmful to man. However, mammals frequently add pathogenic organisms to water sources via intestinal excrement. Epidemiological studies have established beyond a doubt that there is a strong correlation between the presence of waterborne pathogenic organisms and the presence of micro-organisms of intestinal origin. Thus, if pathogens are present in a water source, it is almost certain that non-pathogenic intestinal microorganisms will also be present, generally in much greater concentrations. (On the other hand, the presence of non-pathogenic intestinal organisms does not necessarily imply the presence of pathogenic organisms.)

Of the intestinal organisms present in man, the largest concentration are those bacteria classified as members of the family Enterobacteriaceae. This family consists of five tribes: (1) Eschericheae; (2) Eriwineae; (3) Serrateae; (4) Proteae; and (5) Salmonelleae. Of these tribes, the Eschericheae are the most abundant. Eschericheae are further categorized into three genera: (1) Escherichia; (2) Aerobacter; and (3) Klebsiella. Genera are further classified into species, e.g., *Escherichia coli, Escherichia freundii, Enterobacter aerogenes, Aerobacter cloacae*, etc.

In order to avoid the problem of analyzing for each of the various species of organism present in water, sanitarians have elected to test for those members of the Enterobacteriaceae family that are gram negative and lactose fermenting. These bacteria are classified as coliform bacteria, without attempting further classification. Of the species meeting these criteria members of the genus Escherichia are the most common, with *Escherichia coli* predominant.

There is probably no single bacteriological test more frequently performed than that of the examination of water. Yet, with all the vast amount of testing being performed daily, the evaluation still takes anywhere from three to forty eight hours per analysis. A more rapid methodology for bacterial contamination testing appears to be a desirable goal for any application wherein water sanitation may be a problem.

The term "rapid" appears to have varying meanings to microbiologists. The literature lists many papers claiming rapid analysis techniques, where rapid is defined as less than twenty four hours. The present invention relates to a system in which analysis requires less than two hours, preferably less than one hour.

In addition to analysis speed, a water analysis methodology must be specific to coliforms and sensitive enough to detect a bacterial contamination level of 200 bacteria per 100 ml of water or less. Presently available methodologies will not meet the specificity, sensitivity and speed requirements mentioned above.

The standard procedure for bacterial examination of water is given in the American Public Health Association (APHA) publication "Standard Methods for the Examination of Water and Waste Water." The recommended colifirm bacteria detection test procedure consists of a series of three tests: a presumptive test, a confirmed test and a completed test. The presumptive test is a screening test that depends upon the ability of coliform bacteria to oxidize lactose with the production of $CO_2$ and $H_2$. The confirmed test attempts to eliminate the bacteria that give false-positive results in the presumptive test. Suspicious results of the confirmed tests are further examined in the completed test to confirm or negate the presence of coliforms. All tests require incubation of a sample to produce an adequate quantity of bacteria for visual analysis of the end result.

There are a number of variations of the APHA test procedure commercially available. However, these also involve long incubation periods.

In addition to the APHA procedure for the detection of coliforms, there are a number of other bacterial detection procedures that have been noted in the literature. Among these are:

a. Radiometric methodologies;
b. Electrochemical methodologies;
c. Chromatographic methodologies;
d. Chemiluminescence methodologies; and
e. Fluorescence methodologies.

Radiometric techniques for coliform detection generally follow the APHA culturing technique with the exception that radioactive $C^{14}$ labelled lactose is used. It has been reported that one bacterium can be detected in eight hours.

Electrochemical techniques are somewhat more varied in their detection methodology. Sensitivity of the electrochemical methods are such that reaction times $>3$ hours and bacterial densities of $>10^5$ per ml are required for detection.

Chromatographic methodologies are based upon the chemical differences of various types of bacteria. In general, the chromatographic methodologies require $>4$ hours of culturing to achieve a large enough sample of bacteria for analysis. Also, the technique is probably too difficult to be handled, except by skilled laboratory personnel.

Chemiluminescent methodologies are based upon the presence within bacteria of certain chemicals that either catalyze a light emitting reaction or participate in the reaction. The luminol peroxide reaction is an example of the former, catalyzed by bacterial porphyrins. The luciferin-bacterial ATP (adenosine triphosphate) reaction is an example of the latter. Both reactions are rapid but non-specific. Further, bacterial concentrations $>10^3$/ml are required.

There are several flourescent methodologies that have been reported. The use of fluorescent antibodies represents a prime example of a sensitive, specific bacterial analysis test method. Unfortunately, though sensitive, the flourescent antibody technique is much too specific, i.e., it will detect single strains of bacteria but not a mixture of many strains.

A second approach to the use of fluorescence for bacteria detection uses the reaction between fluorescent substrates for bacterial enzymes. In this case, a fluorescent molecule is chemically attached to a bacterial enzyme substrate. In its attached state it is non-fluorescent. However, once reacted upon by the enzyme, the fluorescent molecule is released and can be caused to fluoresce.

A large variety of enzyme-substrate reactions are analyzed by this approach. The reaction between the coliform enzyme β-D-galactosidase and fluorescein-di-(β-D-galactopyranoside) is one example.

Boris Rotman has developed a technique for detecting a coliform enzyme, β-D-galactosidase, at the single molecule level. This enzyme is the key enzyme permitting coliform bacteria to react with galactosides such as lactose, i.e., lactose $\xrightarrow{\beta\text{-}D\text{-}galactosidase}$ galactose + glucose. Since the ability to ferment lactose is the primary test for classifying bacteria as coliforms or non-coliforms, the presence or absence of β-D-galactosidase in a bacterium provides a convenient method of coliform detection.

Rotman's technique involves the use of a fluorescent reagent that acts as a substrate for β-D-galactosidase. The reagent is fluorescein-di-(β-D-galactopyranoside). When this reagent is hydrolyzed by bacterial β-D-galactosidase, the fluorescein portion of the molecule is released. Fluorescein, being a highly fluorescent material, is readily detected at the part per billion level.

Fluorescein, produced by the hydrolysis reaction, rapidly diffuses out of a coliform bacterium. Even at the part per billion detection level, if the fluorescein is allowed to diffuse into a volume of water, orders of magnitude larger than a bacterium, the concentration of fluorescein will be orders of magnitude lower than the detection limit. Rotman solved this dilution problem by containing small numbers (1–5) of *E. coli* within microdroplets of water. The microdroplets are in turn surrounded by silicone oil in which the fluorescein is insoluble. Thus, all of the fluorescein produced is contained within a very small volume, typically $10^{-12}$ liters per droplet.

The minimum number of molecules of fluorescein that can be detected, based upon a convervative $10^{-5}$ moles per liter detection limit and a $10^{-12}$ liter droplet size, is estimated at $6.023 \times 10^6$ molecules using the relationship:

$$n = A \cdot \alpha \cdot v \qquad (1)$$

where n = minimum number of molecules required for detection

A = Avogadro's number—$6.023 \times 10^{23}$ molecules per mole

α = detection limit—moles per liter v = volume of sample—liters

The time required to form $6.023 \times 10^6$ molecules of fluorescein can be estimated at about 100 seconds from the turnover rate of the β-D-galactosidase molecule (i.e., the number of molecules of lactose hydrolyzed per second) and a knowledge of the average number of enzyme molecules per bacterium.

$$t = n/\phi \cdot \rho \qquad (2)$$

where t = time required

φ = turnover of β-D-galactosidase—120 molecules per second

ρ = number of molecules of enzyme per bacterium—500

Thus, by the use of a highly specific reagent and a simple technique for concentrating the fluorescent product of that reagent's reaction, it is possible to detect single coliform bacteria in reaction times of less than 5 minutes. In fact, the technique is so sensitive that *single molecules* of enzyme, entrapped within microdroplets, can be detected in less than 10 hours of reaction time.

While the Rotman technique is sensitive, it is time consuming and requires skilled personnel. It is an object of the present invention to provide a method and apparatus for quantification of bacteria which can be performed rapidly and by unskilled personnel. By "rapidly" is meant less than two hours at a bacteria level of 200 per 100 ml of water or less. The foregoing and other objects which will be apparent to those having ordinary skill in the art are achieved by the present invention, a description of which follows.

BRIEF SUMMARY OF THE INVENTION

In accordance with the present invention, a liquid sample to be tested for the presence of bacteria is admixed with an enzyme-inducing agent which induces the production, in the bacteria, of an enzyme which is capable of reacting with a fluorescent conjugate ingested by the bacteria to release the fluorescent portion thereof, the amount of the enzyme which is produced being at least sufficient to effect release of the fluorescent portion. The liquid sample is then admixed with a fluorescent conjugate capable of being ingested by the bacteria for reaction with the enzyme to release the fluorescent portion of the fluorescent conjugate. The liquid sample is then formed into microdroplets and dispersed in a liquid carrier such that the released fluorescent portion of the fluorescent conjugate is retained in the microdroplets. The microdroplets are carried in the liquid carrier and the liquid carrier is formed into a stream such that the microdroplets align themselves in the stream. The stream is then moved relative to a fluorescence detector for detecting the fluorescent matter in the microdroplets as they move past the detector. Apparatus for effecting the method is readily automated for operation by unskilled personnel.

DETAILED DESCRIPTION

There follows a detailed description of preferred embodiments of the invention including the drawings of which:

Figure 1:
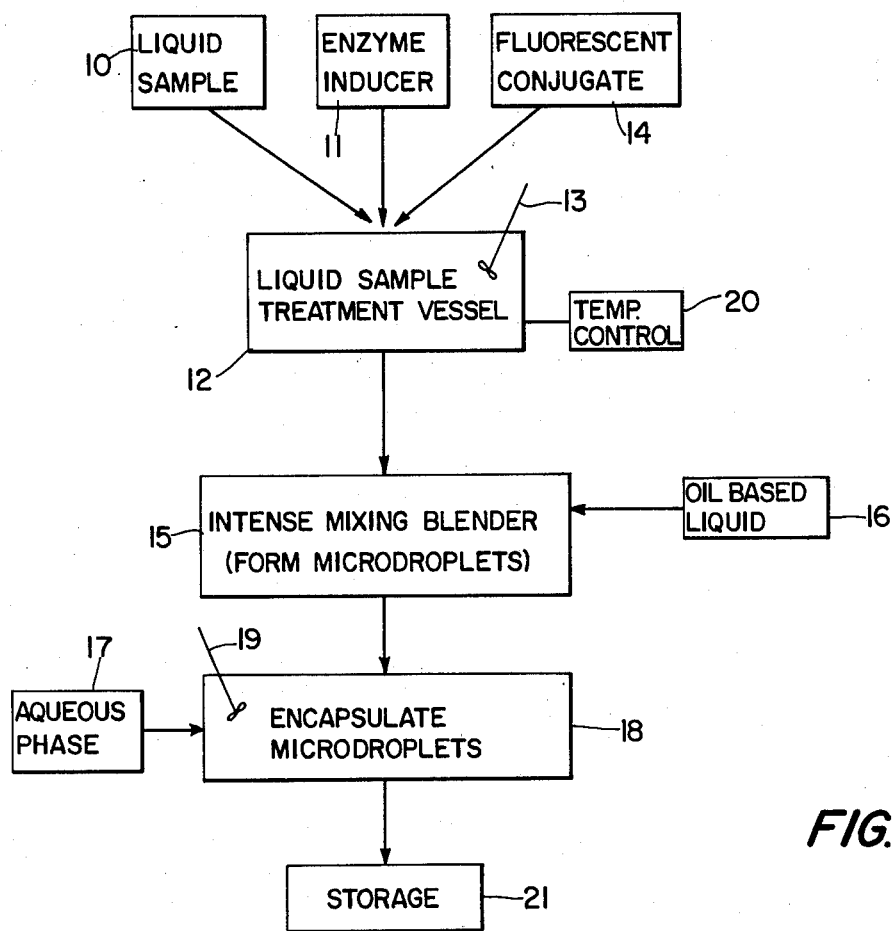
FIG. 1 is a diagrammatic view of apparatus for carrying out the invention.

The bacteria to which the invention is applicable can be any bacteria having an enzymic system that will react with a fluorescent conjugate to release the fluorescent portion of the molecule. By "fluorescent conjugate" is meant a chemical compound which is not itself fluorescent but which contains an enzyme substrate portion and a releasable fluorescent portion which is fluorescent when released by action of the enzyme. The invention has particular applicability to coliform bacteria. Another example is denitrification bacteria, such as described by Mohan et al. in *Biotechnology and Bioengineering*, Volume XVII, pp 1137–1156 (1975). These bacteria contain nitrate and nitrite reductaces and can be used with a nitrate-or nitrite-containing fluorescent conjugate, such as a fluorescein conjugate that can be reduced by the bacteria. The liquid in which the bacteria is found is aqueous and, in particular, water. Among the various aqueous liquids to be tested are natural bodies of water such as rivers, streams, ponds, lakes, estuaries, seas, and the like, and man-made systems such as sewage streams, industrial effluent streams, and the like.

In order to rapidly react with the fluorescent conjugate, the appropriate enzyme should be present in the bacteria in an amount sufficient to cause the fluorescent conjugate to quickly release the fluorescent material. The amount of enzyme required to achieve this result depends, among other things, on the desired speed of release of the fluorescent material, on the intensity of fluorescence of the released fluorescent material, and on the sensitivity of the fluorescence detection system. Since rapid release of the fluorescent material is desirable, it is desirable to induce a large number of enzymes in the bacteria, for example, about 500 or 1000 molecules of enzyme per bacterium. However, inducing large numbers of enzyme molecules requires time and, since rapidity of testing is a basic objective of the invention, it is preferred to reduce induction to a minimum time needed to induce the minimum number of enzymes required to provide sufficiently rapid release of the fluorescent material. If the released fluorescent material is sufficiently intense, and if a detection system is sufficiently sensitive, very few enzymes will be required. In general, using readily available materials and equipment such as described herein, an enzyme level of about 100 molecules per bacterium is sufficient. Using $E.\ coli$ as an example, the enzyme $\beta$-D-galactosidase is naturally present in an amount of 0–10 molecules per bacterium. Accordingly, it is necessary to treat the bacteria to induce the production of the enzyme to the desired level. Production of the enzyme can be induced by any of several suitable chemical agents such as lactose or a structurally related chemical compound.

Among the chemical inducers are the galactosides that are also substrates for the enzyme. Suitable inducing agents include methyl-$\beta$-thiogalactoside and isopropyl thio $\beta$-D-galactopyranoside. Other suitable inducers include those disclosed in "Methods in Enzymology" Volume 22, page 86 (1971). By the use of induction, the number of molecules of enzyme is increased to an appropriate level of at least 500 molecules per bacterium. This can be done rapidly, generally in less than 15 minutes. Inducement of enzyme production is readily accomplished by admixing the liquid sample and the inducing agent.

By the term "fluorescent conjugate" is meant a chemical agent which is itself non-fluorescent but which contains a fluorescent portion, such as fluorescein, which, when released from the parent compound, is fluorescent and contains an enzyme substrate portion which renders the agent capable of reaction with the induced enzyme to effect release of its fluorescent portion. It will be readily apparent that the selection of the fluorescent conjugate is dependent upon the enzyme that is induced in the bacteria. In the case of $E.\ coli,$ the induced enzyme is preferably $\beta$-galactosidase and a suitable fluorescent conjugate is fluorescein di-$\beta$-D-galactopyranoside. Other bacteria, of course, have other enzymic systems that will react with a fluorescent conjugate to release its fluorescent portion. For example, denitrification bacteria contain nitrate and nitrite reductase enzymes. A suitable fluorescent conjugate is one containing nitrate or nitrite reducible by the bacteria to release the fluorescent portion of the conjugate. Other suitable fluorescent conjugates include fluorescein-di-(2', 3', 4', 6'-tetra-O-acetyl-$\beta$-D-galactopyranoside), 3-O-methyl-fluorescein-2', 3', 4', 6'-tetra-O-acetyl-$\beta$-D-galactopyranoside, and monocyclohexylammonium 3-O-methyl-fluorescein phosphate.

The liquid sample may be formed into microdroplets in any convenient manner such as spraying, atomizing, encapsulation, emulsification, and the like. The microdroplets are then dispersed in a liquid carrier, preferably aqueous. The preferred technique is to encapsulate microdroplets of the liquid sample with a material substantially impermeable to the fluorescent material such that the fluorescent portion of the fluorescent conjugate is retained within the microdroplet after it is released by reaction with the bacterial enzyme. The appropriate size of a microdroplet is a function of the detection limit of the fluorimetry system, the concentration of the bacterial enzyme and other factors. The more concentrated the bacteria, and the induced bacterial enzyme, the more fluorescent matter is released upon reaction with the fluorescent conjugate, and vice versa. In general, therefore, the size of the microdroplet is keyed to the detection level of the system. In general, however, a microdroplet size of from $10^{-12}$ to $10^{-9}$ ml is suitable.

The preferred encapsulation technique is preferably carried out in accordance with the technique disclosed in U.S. Pat. No. 3,779,907, the disclosure of which is incorporated herein by reference. In this technique, the aqueous liquid sample to be encapsulated is added relatively slowly (over a few minutes) to an oil based liquid under conditions of intense mixing. Examples of the oil based liquid are given in the patent. An example of a suitable oil based liquid is 2% sorbitan monooleate in a high molecular weight isoparaffin having a carbon number range of 25 to 35. Another example is 93% isoparaffin lubricating oil, 4.5% polyisobutylene, 2.0% sorbitan monooleate, and 0.5% of a high molecular weight polyamine. A Waring blender or the like is suitable for this intense mixing. The liquid at the end of this step is an emulsion. The aqueous solution to be encapsulated is present in small droplets surrounded by the continuous oil phase. The emulsion is then added to a liquid carrier, with which the oil based liquid is immiscible, under gentle agitation which causes rapid formation of microdroplets in the liquid carrier, the microdroplets being made up of the liquid sample droplets encapsulated in a liquid, oil phase, membrane. Encapsulated microdroplets having a diameter of 1–100 $\mu$ are readily produced in this manner. The technique is also reported in "Exxon Company Report AK-1-73-2224" Asher et al., May 10, 1974, herein incorporated by reference.

As mentioned above, other techniques may be used to form the microdroplets. Irrespective of the technique used to form the microdroplets, they are dispersed in a liquid carrier in which the droplets, or the encapsulated droplets, are substantially insoluble. It is also important that the components of the liquid sample—bacteria, enzymes, fluorescent conjugate, fluorescent matter, etc.—are retained in the microdroplets. Accordingly, where encapsulation is not employed, the components of liquid sample should be substantially insoluble in the carrier liquid and, where encapsulation is employed, the capsule wall material should be substantially impermeable to those components.

The microdroplets may be dispersed in the liquid carrier in any convenient manner such as by gentle stirring.

After the microdroplets have been dispersed in a liquid carrier, the liquid carrier is formed into a stream such that the microdroplets are aligned therein. A suitable device for effecting this step is shown in FIG. 1 which also illustrates apparatus for carrying out the steps described above in connection with encapsulation of the microdroplets.

Liquid sample reservoir 10 and enzyme inducer reservoir 11 are provided to supply a liquid sample to be tested for bacteria and an enzyme producing agent to a liquid sample treatment vessel 12 by means of suitable valves and/or pumps, not shown. A stirrer 13 is provided to facilitate admixture of the materials. A fluorescent conjugate, conveniently provided in solution, is admixed at any convenient time from reservoir 14. The fluorescent conjugate may be conveniently added at the same time as the enzyme inducing agent. After admixture with enzyme inducer and fluorescent conjugate, the liquid sample is formed into microdroplets by intense mixing in a blender 15 with an oil base liquid 16 to form an emulsion as described above. The microdroplets are then dispersed in a liquid carrier by admixing the emulsion with an aqueous phase 17 in a vessel 18 provided with an agitator 19. Vessels 12, 15 and/or 18 are provided with temperature control means for controlling temperature to induce production of the enzyme. This is conveniently carried out by controlling temperature in a vessel 12 by means of a conventional control device 20 prior to introduction of the fluorescent conjugate. After admixture of the fluorescent conjugate, the liquid sample is held, for example after formation of the encapsulated microdroplets, for a sufficient period of time to effect reaction of the fluorescent conjugate and the release of the fluorescent matter in the microdroplets. A storage vessel 21 is readily provided for this purpose.

The liquid carrier containing the dispersed microdroplets of liquid sample (which microdroplets now contain fluorescent matter to an extent dependent upon the content in the original liquid sample of the bacteria in question) is then formed into a stream in which the microdroplets are aligned by being moved into and through a tube 22 carried in a flow chamber 23. An outer tube 24 may be provided for an annular flow of a sheath liquid surrounding the stream of carrier liquid formed in tube 22. The diameter of tube 22 is such that the microdroplets align themselves and, for this purpose, a diameter of slightly larger than the largest microdroplets up to two or three times that size is preferred. A conventional fluorescence sensor 25 is provided adjacent tube 22 to detect fluorescence in the microbubbles as they pass a detection zone 26 of tube 22 illuminated by a fluorescence excitation light source 27. A conventional lens 28 and filters 29 and 30 are interposed between the detection zone 26 and detector 25.

Figure 2:
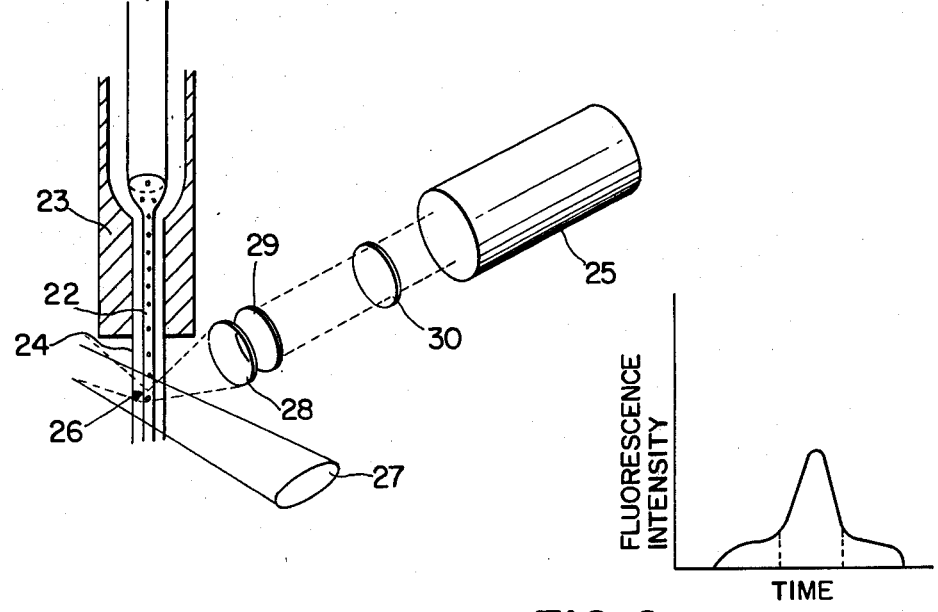
FIG. 2 is a graph showing the intensity of detected fluorescence as a function of time.

FIG. 2 is a graphical illustration of the intensity of fluorescence detected by sensor 25 as a function of time as a fluorescent microbubble passes detector zone 26. The detected fluorescence provides a ready means of determining the bacterial content of the original liquid sample. The original liquid sample is usually small, such as 1 ml, and is entirely encapsulated. Each microdroplets which contains live bacteria will exhibit fluorescence and thus give a cell count. Since the entire 1 ml sample is counted, no concentration of the sample is required. However, the original liquid sample may be concentrated if desired. Further, the effect of suspended solids will be minimal since only fluorescent microdroplets will be counted. Induced coliforms will have essentially the same amount of induced enzyme in each bacterium. Accordingly, the fluorescence produced by each induced bacterium will be substantially the same. Accordingly, two induced bacteria per droplet produce twice the fluorescence of a droplet containing one bacterium. Three induced bacteria produce three times the fluorescence, and so on. Accordingly, by counting both the number of droplets and by measuring the amplitude of fluorescence of each, the total fluorescence can be measured and this can be used to measure the bacteria content of the original liquid sample. The fluorescence detection system can be readily calibrated, such as by comparison with results from control samples having known bacteria count.

Various additional materials may be added to the liquid sample being tested. For example, where a particular class of bacteria, such as coliform bacteria, is under investigation, an agent may be added to suppress growth of other bacteria. Another useful additive is an agent, such as isoamyl alcohol, which perforates the bacterial cell membranes and thus facilitates diffusion of the fluorescent conjugate into, and the diffusion of the liberated fluorescent material out of, the bacterial cells.

If desired, the system can be rendered more specific to the determination of fecal coliform bacteria by effecting enzyme inducement at a temperature of 44.5° C. rather than at 37° C. At the higher temperature, inducement of the $\beta$-D-galactosidase is inhibited in non-fecal coliform bacteria. In addition to temperature, chemical agents such as Brilliant Green dyestuff or bile salts may be added to increase selectivity of *E. coli*.

EXAMPLE

The following reagents are mixed:
A. Lactate medium
  $K_2HPO_4$: 6.968 g
  $KH_2PO_4$: 4.082 g
  $(NH_4)_2SO_4$: 1.004 g
  $MgSO_4 \cdot 7H_2O$: 0.098 g
  Distilled Water: 1000 ml
  Casamino Acids: 0.040 g
  Sodium lactate: 0.4% by volume
B. Induction Medium
  Isopropyl thio $\beta$-D-galactopyranoside (IPTG) $5 \times 10^{-4}$ M in lactate medium.
C. Fluorescent conjugate
  Fluorescein-di-($\beta$-D-galactopyranoside) FDG $2 \times 10^{-3}$ M in lactate medium. (FDG is purified by paper chromatography.)
D. Liquid membrane oil based liquid
  An oil based liquid in accordance with Example 1 of U.S. Pat. No. 3,779,907 is prepared by adding 2% sorbitan monooleate surfactant (Span 80) and a high molecular weight isoparaffin having a carbon number range of from about 25 to 35.

A 100 ml sample of water to be tested for coliform bacteria is taken from a river at a location downstream of a sewage treatment plant having an effluent stream discharging into the river. After filtration to remove suspended solids, a one ml sample of the larger sample is admixed with 10 μl of the IPTG enzyme induction medium and induction is allowed to proceed for about 15 to 30 minutes. The liquid sample is cooled to a temperature of about 5° C. and the fluorescent conjugate reagent is added in an amount such that the final concentration of FDG is $1.5 \times 10^{-4}$ M. The liquid sample is then admixed in a Waring blender with an approximately equal volume of liquid membrane oil based liquid reagent to form an emulsion of the liquid sample in the oil based liquid. The emulsion is then added with gentle stirring into a volume of about 3 ml of water to disperse therein encapsulated droplets having a diameter of about 20μ. The volume of water containing the encapsulated droplets is then fed through a tube 22 having a diameter of about 100μ, and the fluorescence in the microbubbles is induced by excitation light source 27 is detected by sensor 25. By comparison with results obtained from known controls, the bacterial content of the original liquid sample is determined.

What is claimed is:

1. A method of rapidly detecting and quantifying bacteria present in a liquid sample comprising the steps of:
  admixing with a liquid sample to be tested for the presence of bacteria an enzyme-producing agent which induces the production of an enzyme in said bacteria, said enzyme being capable of reacting with a fluorescent conjugate ingested by said bacteria to release the fluorescent portion thereof, to induce production of said enzyme in an amount sufficient to effect release of said fluorescent portion;
  admixing said liquid sample and a fluorescent conjugate capable of being ingested by said bacteria for reaction with said enzyme to release the fluorescent portion of said fluorescent conjugate;
  forming microdroplets of said liquid sample encapsulated by a oil base liquid membrane in a liquid carrier, in which said encapsulated microdroplet are substantially insoluble, each of said encapsulated microdroplets retaining the fluorescent matter released from said fluorescent conjugate;
  forming said liquid carrier into a stream such that the encapsulated microdroplets align themselves therein; and
  moving said stream relative to a detector for detecting the fluorescent matter in the encapsulated microdroplets to detect the presence of said bacteria in the liquid sample, detecting fluorescent matter in said microdroplets, measuring the total fluorescence and determining the bacterial content in said liquid sample.

2. A method according to claim 1 wherein said bacteria are coliform bacteria.

3. A method according to claim 2 wherein said enzyme comprises $\beta$-D-galactosidase.

4. A method according to claim 3 wherein said fluorescent conjugate comprises fluorescein-di-($\beta$-D-galactopyranoside) and wherein said fluorescent portion comprises fluorescein.

5. A method according to claim 1 wherein said microdroplet size is from $10^{-12}$ to $10^{-9}$ ml.

6. A method according to claim 1 including the preliminary step of concentrating a liquid to be tested to provide said liquid sample.

7. A method according to claim 1 including the further step of admixing into said liquid sample an agent which suppresses growth of non-coliform bacteria which may be present therein.

8. A method according to claim 1 including the further step of determining the amount of fluorescent matter in said microbubbles to determine the amount of coliform bacteria present therein.

9. A method according to claim 1 wherein said liquid comprises water.

10. A method according to claim 1 wherein the admixture of said liquid sample and said enzyme-producing agent is effected under conditions to effect production of said enzyme in fecal coliform bacteria and to inhibit production of said enzyme in non-fecal bacteria.

11. A method according to claim 10 wherein said enzyme comprises $\beta$-D-galactosidase and wherein the production of said enzyme is effected at a temperature of 44.5° C.

12. A method according to claim 1 wherein said microbubbles are encapsulated within a material substantially impermeable to the fluorescent matter whereby the fluorescent matter is retained therein.

13. A method according to claim 1 wherein the enzyme is present in an amount of 100 molecules per bacterium.

14. Apparatus for rapidly detecting bacteria present in a liquid sample comprising:
  means for admixing a liquid sample to be tested for the presence of bacteria and an enzyme-producing agent which induces the production of an enzyme in said bacteria, said enzyme being capable of reacting with a fluorescent conjugate ingested by said bacteria to release the fluorescent portion thereof and for admixing said liquid sample and a fluorescent conjugate capable of being ingested and hydrolyzed by said bacteria for reaction with said enzyme to release the fluorescent portion of said fluorescent conjugate;
  means for storing the admixture of liquid sample and enzyme-producing agent under controlled conditions to effect production of said enzyme;
  means for forming microdroplets of said liquid sample encapsulated by an oil base liquid membrane in a liquid carrier in which said encapsulated microdroplets are substantially insoluble;
  means for forming said liquid carrier containing said microdroplets into a stream such that the microdroplets align themselves therein;
  means for detecting fluorescence;
  means for moving said stream relative to said fluorescence detector means to detect the presence of said bacteria in said liquid sample.

15. Apparatus according to claim 14 further comprising means for controlling the temperature of the admixed liquid sample and enzyme producing agent.

* * * * *